United States Patent [19]
Hood et al.

[11] Patent Number: 5,324,297
[45] Date of Patent: Jun. 28, 1994

[54] ULTRASONIC TOOL CONNECTOR

[75] Inventors: Larry L. Hood, Laguna Hills; James T. Caillouette, Newport Beach; Robert C. Klapper, Los Angeles; Gregg Hughes, El Toro; Ted Carlson, Mission Viejo, all of Calif.; John Berkman, Grants Pass, Oreg.

[73] Assignee: Advanced Osseous Technologies, Inc., Aliso Viejo, Calif.

[21] Appl. No.: 665,418

[22] Filed: Mar. 5, 1991

Related U.S. Application Data

[63] Continuation-in-part of Ser. No. 304,820, Jan. 31, 1989, Pat. No. 5,019,083.

[51] Int. Cl.⁵ .............................................. A61B 17/32
[52] U.S. Cl. ........................................ 606/99; 606/169; 606/79; 604/22
[58] Field of Search ............... 411/417, 418, 437, 386, 411/553, 549, 349; 606/79, 84, 85, 99, 169; 604/22

[56] References Cited

U.S. PATENT DOCUMENTS

| | | |
|---|---|---|
| 33,530 | 10/1861 | Leisen . |
| 165,403 | 7/1875 | Blatt . |
| 446,078 | 2/1891 | Rouse . |
| 804,831 | 11/1905 | Cunnius . |
| 1,096,763 | 5/1914 | Smith . |
| 1,390,904 | 9/1921 | Hazelton . |
| 1,451,970 | 4/1923 | Taylor . |
| 1,483,164 | 2/1924 | Driggs . |
| 1,967,145 | 7/1934 | Fisher . |
| 2,138,245 | 11/1938 | Smith . |
| 2,257,327 | 4/1941 | Bradford . |
| 2,517,364 | 8/1950 | Torresen ................. 411/437 X |
| 2,714,890 | 8/1955 | Vang . |
| 2,784,637 | 3/1957 | Smisko . |
| 2,828,662 | 4/1958 | Antal . |
| 2,840,404 | 6/1958 | Weber, Jr. . |
| 3,006,003 | 10/1961 | Johnson, Jr. . |
| 3,076,904 | 2/1963 | Kleesattel et al. . |
| 3,086,288 | 4/1963 | Balamuth et al. . |
| 3,101,210 | 8/1963 | Johnson ................. 411/386 X |
| 3,184,353 | 5/1965 | Balamuth et al. . |
| 3,346,279 | 10/1967 | Stachiw et al. . |
| 3,401,446 | 9/1968 | Obeda et al. . |
| 3,407,454 | 10/1968 | Myatt ................. 411/549 |
| 3,526,219 | 9/1970 | Balamuth . |
| 3,589,363 | 6/1971 | Banko et al. . |
| 3,683,736 | 8/1972 | Loose . |
| 3,693,613 | 9/1972 | Kelman . |
| 3,710,641 | 1/1973 | Anderson . |
| 3,809,977 | 5/1974 | Balamuth et al. . |

(List continued on next page.)

FOREIGN PATENT DOCUMENTS

| | | |
|---|---|---|
| 1014454 | 7/1977 | Canada ................. 411/417 |
| 121491 | 3/1983 | European Pat. Off. . |
| 133393 | 2/1985 | European Pat. Off. . |
| 243298 | 4/1986 | European Pat. Off. . |
| 0424231 | 4/1991 | European Pat. Off. . |
| 2741107 | 9/1977 | Fed. Rep. of Germany . |

(List continued on next page.)

OTHER PUBLICATIONS

"Theory and Analysis of Sectional Concentrators" by L. G. Merkulov and A. V. Kharitonov, Apr. 18, 1958.
"Mechanical Transformers for Producing Very Large Motion" by E. A. Neppiras, Acustica, vol. 13, Mar. 26, 1963.

(List continued on next page.)

*Primary Examiner*—Robert A. Hafer
*Assistant Examiner*—David Kenealy
*Attorney, Agent, or Firm*—Knobbe, Martens, Olson & Bear

[57] ABSTRACT

Disclosed is a mechanical junction for facilitating the rapid attachment and removal of ultrasonic surgical components for the transfer of ultrasonic energy across the junction from an ultrasonic transducer to an ultrasonically activated tool bit. The junction achieves a high, evenly distributed compressive force to optimize propagation of the ultrasonic energy from the transducer to a tool bit, while maintaining a relatively small outside diameter of the ultrasonic tool.

22 Claims, 6 Drawing Sheets

U.S. PATENT DOCUMENTS

| | | |
|---|---|---|
| 3,823,717 | 7/1974 | Pohlman et al. |
| 3,862,630 | 1/1975 | Balamuth |
| 3,889,166 | 6/1975 | Scurlock |
| 3,902,495 | 9/1975 | Weiss et al. |
| 3,990,452 | 11/1976 | Murry et al. |
| 4,041,947 | 8/1977 | Weiss et al. |
| 4,056,761 | 11/1977 | Jacoby et al. |
| 4,063,557 | 12/1977 | Wuchinich et al. |
| 4,184,510 | 1/1980 | Murry et al. |
| 4,188,952 | 2/1980 | Loschilov et al. |
| 4,248,232 | 2/1981 | Engelbrecht et al. |
| 4,260,180 | 7/1981 | Halushka |
| 4,277,710 | 7/1981 | Harwood et al. |
| 4,298,074 | 11/1981 | Mattchen |
| 4,418,583 | 12/1983 | Taig |
| 4,425,115 | 1/1984 | Wuchinich |
| 4,600,343 | 7/1986 | Frerejacques ............... 411/386 X |
| 4,636,219 | 1/1987 | Pratt et al. |
| 4,679,959 | 7/1987 | Cavallaro |
| 4,686,971 | 8/1987 | Harris et al. |
| 4,705,038 | 11/1987 | Sjostrom et al. |
| 4,705,500 | 11/1987 | Reimels et al. |
| 4,750,488 | 6/1988 | Wuchinich et al. |
| 4,768,496 | 9/1988 | Kreizman et al. |
| 4,778,469 | 10/1988 | Lin et al. |
| 4,781,507 | 11/1988 | Duenas |
| 4,828,566 | 5/1989 | Griss |
| 4,832,683 | 5/1989 | Idemoto et al. |
| 4,834,081 | 5/1989 | Van Zile |
| 4,846,161 | 7/1989 | Roger |
| 4,850,755 | 7/1989 | Spencer et al. |
| 5,019,083 | 5/1991 | Klapper et al. |

FOREIGN PATENT DOCUMENTS

| | | |
|---|---|---|
| 2083148 | 12/1971 | France |
| 2508306 | 12/1982 | France |
| 2614524 | 4/1987 | France |
| 8802250 | 4/1988 | PCT Int'l Appl. |
| 9004362 | 5/1990 | PCT Int'l Appl. |
| 9111965 | 8/1991 | PCT Int'l Appl. |
| 9202658 | 2/1992 | PCT Int'l Appl. |
| 659798 | 3/1977 | U.S.S.R. |
| 929088 | 5/1982 | U.S.S.R. |
| 1229467 | 8/1984 | U.S.S.R. |
| 692041 | 5/1953 | United Kingdom ............... 411/437 |
| 1371335 | 10/1974 | United Kingdom |
| 2140345 | 11/1984 | United Kingdom |

OTHER PUBLICATIONS

"Complete Replacement Arthroplasty of the Hip by the Ring Prosthesis", The Journal of Bone and Joint Surgery, P. A. Ring, pp. 720–731, (British), vol. 50B, No. 4, Nov. 1968.

"Ultrasonic Cataract Extraction With Acoustic Horn" by Douglas McG. Clarkson and Calbert I. Phillips, Transactions of the Ophthalmological Society of the United Kingdom, (1975), 95,477.

"Femoral Fractures in Conjunction With Total Hip Replacement" by Richard D. Scott, et al., The Journal of Bone and Joint Surgery, vol. 57–A, No. 4, Jun. 1975.

"A Sonic Tool for Spinal Fusion" by Edmund B. Weis, Jr., M.D., Orthopedic Clinics of North America, vol. 8, No. 1, Jan. 1977.

Orthopedic Catalog—Richards Manufacturing Co., Inc., pp. 10, 14 and 20, 1981.

"A New Technique for Removal of Broken Femoral Stems in Total Hip Replacement" by William H. Harris et al., The Journal of Bone and Joint Surgery, vol. 63–A, No. 5, Jun. 1981.

"Piezoelectric Ceramics: Characteristics and Applications" by Don Berlincourt, Acoustical Society of America, vol. 70, No. 6, Dec. 1981.

"A Model System to Demonstrate the Role of Cavitational Activity in Ultrasonic Scaling" by A. D. Walmsky; W. R. E. Laird and A. R. Williams, J Dent Res 63(9):1162–1165, Sep. 1984.

Biological Fixation of the Porocoat AML© Hip—Manual for Pre-Operative Planning and Recommended Surgical Technique, (1984), by Charles A. Engh, M.D. and J. Dennis Bobyn, Ph.D.

"Posterior Lumbar Interbody Fusion Technique: Complications and Pitfalls" by Paul M. Lin, M.D., Clinical Orthopaedics and Related Research, No. 193, Mar. 1985.

"The Stepped Horn" by John F. Belford—Clevite Electronic Components Division of Clevite Corporation, Dec. 12, 1985.

Technical Support Package on "Quick-Connect Heavy-Duty Fastener", NASA TECH BRIEF, vol. 10, No. 2, Item #34, Mar./Apr. 1986.

"Atraumatic Removal of a Well-Fixed Porous Ingrowth Hip Prostehesis" by Shearwood J. McClelland, et al., Orthopaedic Review, vol. XV, No. 6, Jun. 1986.

"The Window Technique for the Removal of Broken Femoral Stems in Total Hip Replacement" John R. Moreland, et al., Clinical Orthopaedics and Related Research, No. 212, Nov. 1986.

"Development of a Bone-Fixation Prosthetic Attachment" by Lester J. Owens, NASA Kennedy Space Center, pp. 281, 283, 285, 287, 289, 291 and 293.

Technical Support Package for Tech Brief LA-R-12232, "Quick-Connect Threaded Attachment Joint", Langley Research Center, NASA.

"Work-in-Progress #1: The Lithotriptor and Its Potential Use in the Revision of Total Hip Arthroplasty" by Robert R. Karpman, et al., Orthopaedic Review, vol. XVI, No. 1, Jan. 1987.

"Controlled Perforation: A Safe Method of Cement Removal from the Femoral Canal" by Sam V. Sydney, et al., Surgical Rounds for Orthopaedics, pp. 17–19, Jan. 1989.

"Proximal Femoral Osteotomy in Difficult Revision Hip Surgery: How to Revise the Unrevisable" by Hugh H. Cameron, Ph.D., Contemporary Orthopaedics, May 1989, vol. 18, No. 5.

"Symposium: Advanced Biomaterials—The Future of Orthopaedics" by John P. Collier, D. E.; Charles A. Engh, M.D.; Jack Lemons, Ph.D., Contemporary Orthopaedics, Aug. 1989, vol. 19, No. 2.

"Femoral Fracture During Non-Cemented Total Hip Arthroplasty", John A. Schwartz, Jr., et al., The Journal of Bone and Joint Surgery, Incorporated, pp. 1135–1142, Sep. 1989, vol. 71–A, No. 8.

OTHER PUBLICATIONS

"Effect of Press-Fit Femoral Stems on Strains in the Femur: A Photoelastic Coating Study", X. M. Zhou et al., The Journal of Arthroplasty, Mar. 1990, vol. 5, No. 1A.

"The Use of Ultrasonic Tools in Revision Arthroplasty Procedures", Contemporary Orthopaedics by Robert C. Klapper, M.D. and James T. Caillouette, M.D., Mar. 1990, vol. 20, No. 3.

Piezoceramics Applications Data (Undated), pp. 3–10.

"Piezoelectric Displacement Generators—Status and Lower Frequencies" by D. Berlincourt, Channel Industries, Inc. (Undated).

*Fracture Appliances* by DePuy, Inc., 1964.

Photographs 1–3 illustrating an ultrasonic aspiration surgical tool used in neural surgery, designed by Dr. David Wuchinich and disclosed in 1967.

Photographs 4–15 illustrating three ultrasonic surgical tools manufactured by Quinton and distributed by Howmedica, Inc. in 1985.

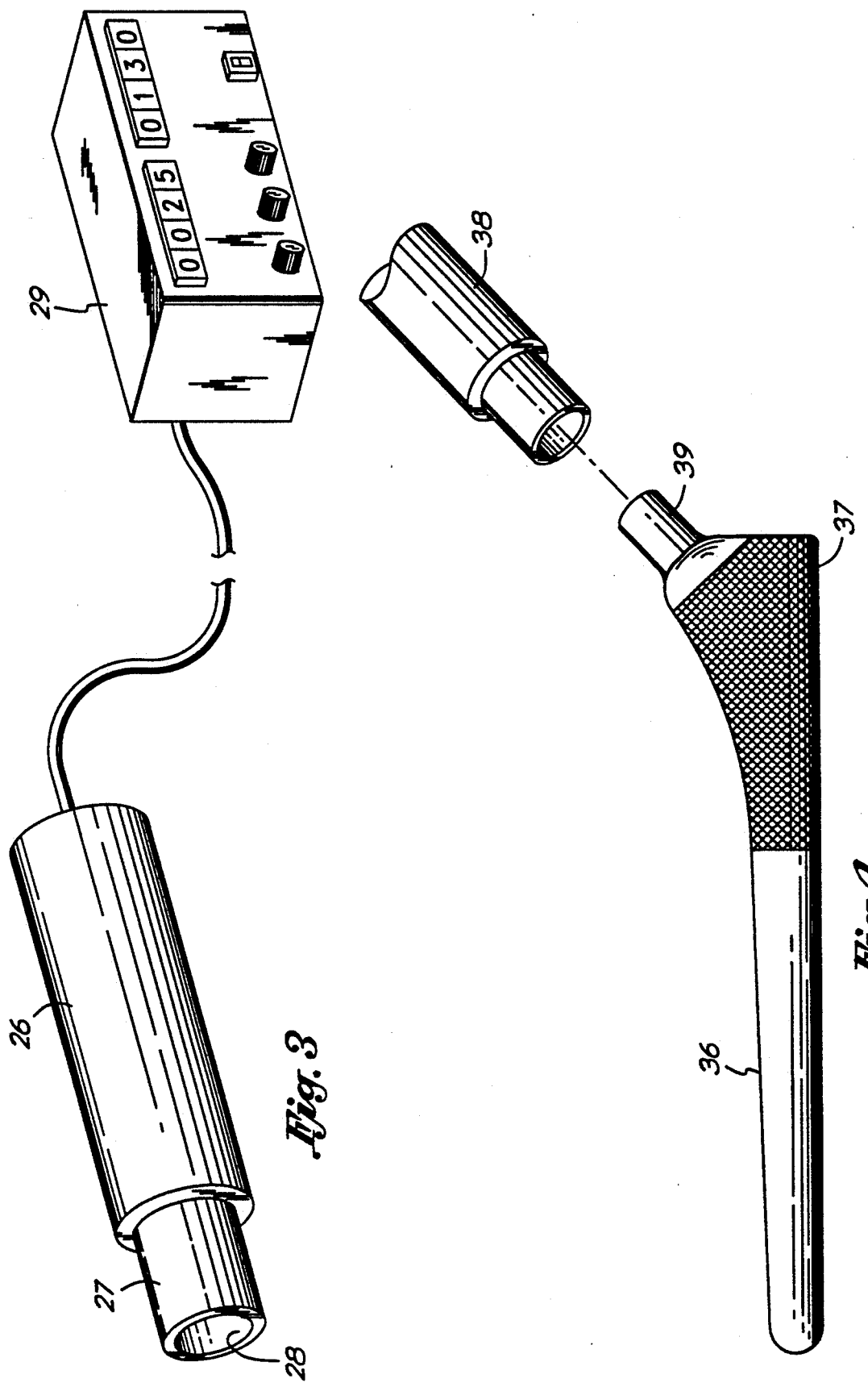

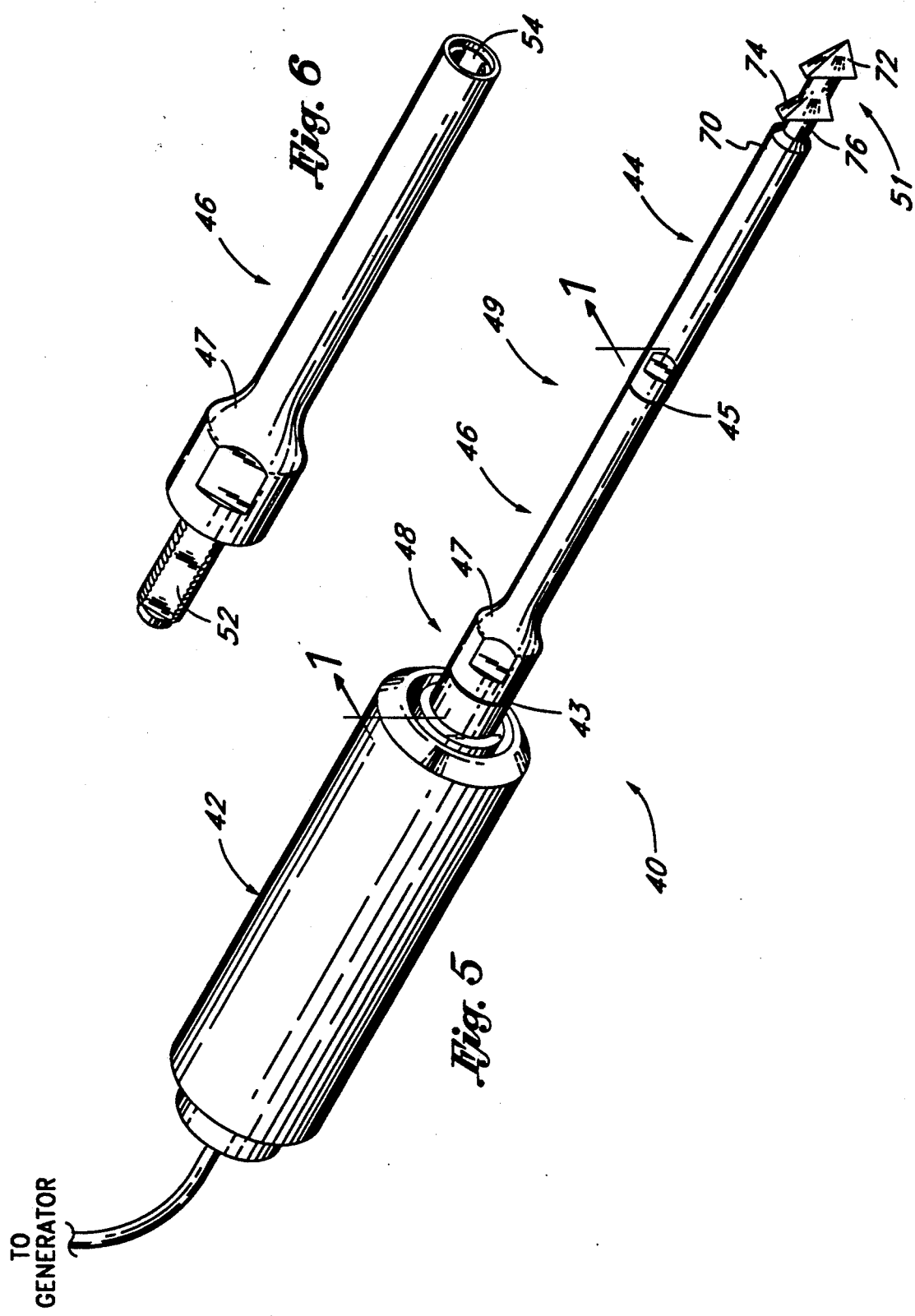

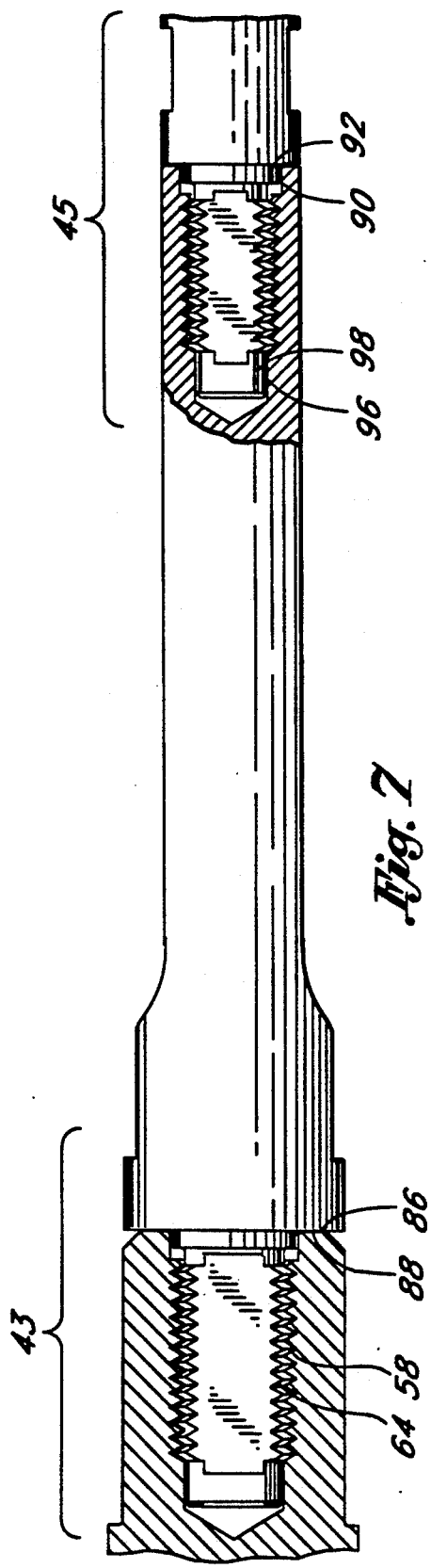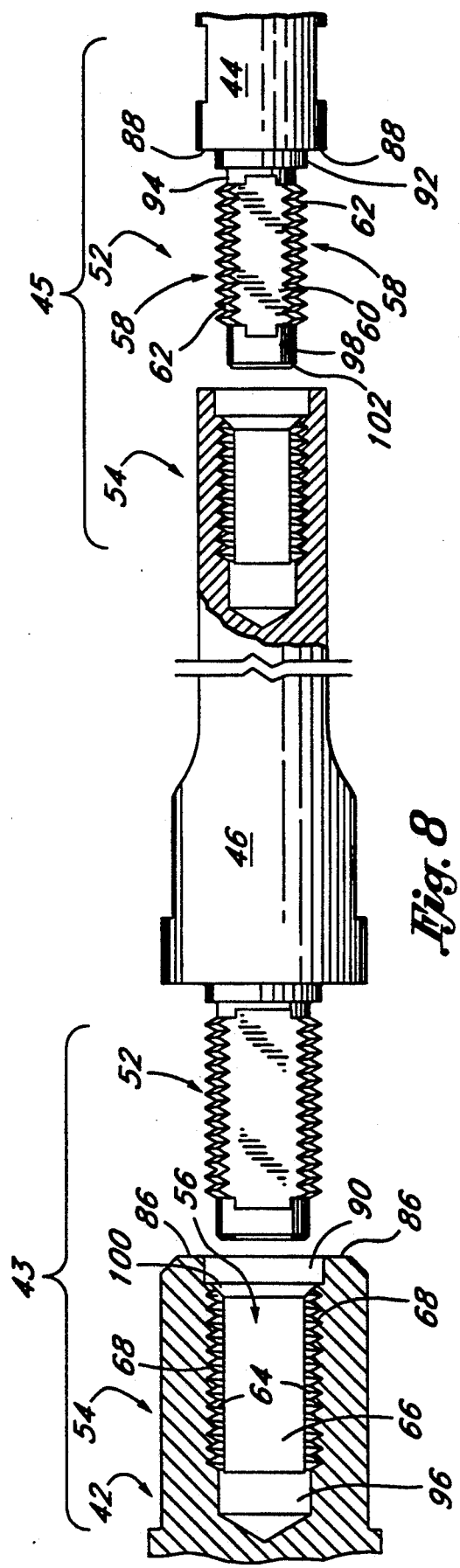

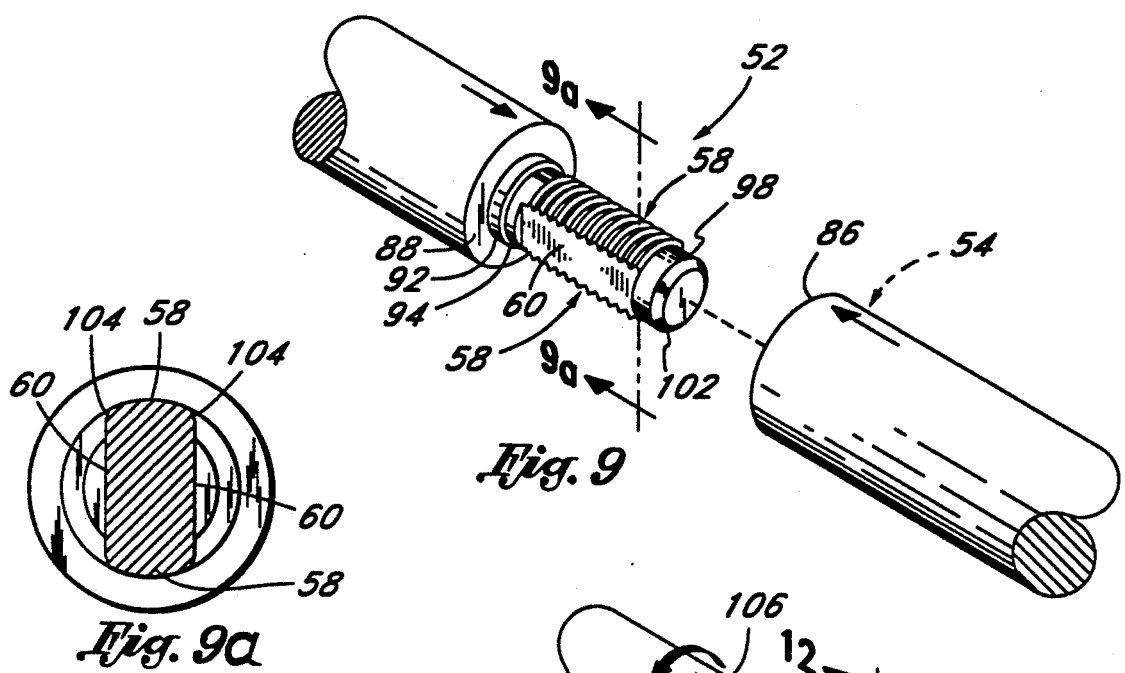
Fig. 9
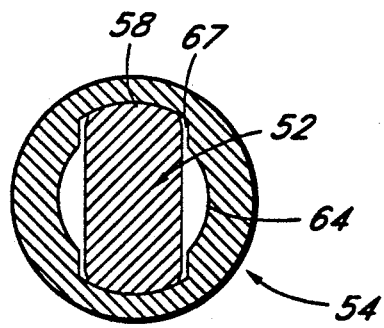
Fig. 9a
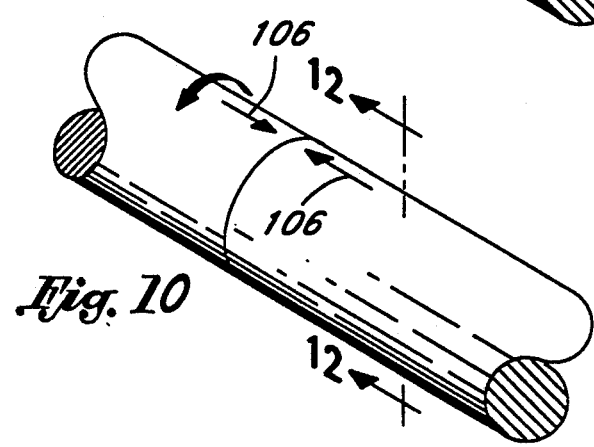
Fig. 10
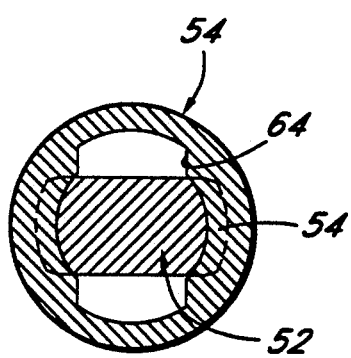
Fig. 12
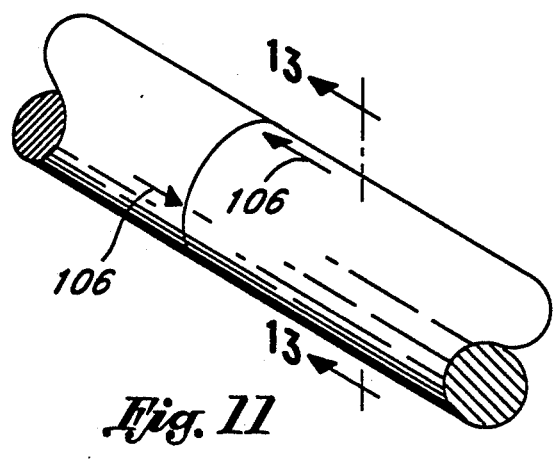
Fig. 11
Fig. 13

ULTRASONIC TOOL CONNECTOR

RELATED APPLICATIONS

The present application is a continuation-in-part of a co-pending application, Ser. No. 304,820, filed Jan. 31, 1989 now U.S. Pat. No. 5,019,083.

FIELD OF THE INVENTION

This invention relates to techniques and apparatus for introducing and removing an orthopedic prosthesis such as a femoral component of a hip joint replacement, acetabular cup, knee joint, shoulder joint, or the like. In particular, this invention relates to quick release ultrasonic tool connectors adapted for use in such procedures.

BACKGROUND OF THE INVENTION

It has been over sixty years since the first use of replacement parts for hip joints. There have been many advances in the prosthetic components, materials, surgical techniques and the like, so that total hip joint replacement has become relatively commonplace. Related techniques have also been used for replacing knee and shoulder joints.

There are two principal components to a hip replacement prosthesis. One is an acetabular cup which is implanted in the acetabulum. The acetabular cup provides a spherical socket which is the bearing surface for the replacement joint. The other component comprises a femoral stem which is fitted into the medullary canal of the femur and a femoral head on the steam having a spherical surface which meets with the acetabular socket.

The femoral portion of the prosthesis is inserted by cutting off the femoral neck with or without removing the greater trochanter. The medullary canal is then prepared using drills, reamers and successively larger rasps to produce a cavity which is closely complementary to the femoral stem. After cleaning, the femoral stem is driven into place in the canal with what is essentially a press fit. Preparing the cavity to fit the stem is tedious and prolongs the period the patient must be kept under anaesthesia.

The femoral stem may be held in place by a polymethylmethacrylate cement (PMMA) or it may be provided with a porous surface on the shank which accommodates ingrowth of cancellous bone which secures the femoral component in the femur.

The acetabular cup is implanted after grinding a socket in the pelvis to receive it. The acetabular cup may be secured with cement, or may be fastened to the bone with screws after a press fit. Similar techniques, differing in detail are used for implanting replacement shoulder joints, knees and the like.

Despite advances in the technology of hip replacement, it is found that a substantial number of "revisions" are required. Such revisions involve removing components of the hip joint and replacing them. Such revisions may be required shortly after the original surgery due to complications. More commonly they occur eight or ten years after the original surgery due to any of a number of problems that may arise. Such revisions are traumatic for the patient, tedious for the surgeon, and quite time consuming for surgical staff and facilities.

A principal problem in revisions is removal of the femoral component. Some such components are made with transverse holes or threaded holes for connection of tools to extract the femoral stem from the medullary canal. Repeated hammer blows may be applied for driving the stem out of the cavity. Sometimes a window is cut in the femoral cortex near the distal end of the shank, and a punch and hammer are used for driving the shank toward the open end of the femur. Trauma to the patient can be severe and breakage of parts of the femur is not unusual. The techniques employed for removing the femoral component have been characterized as barbaric.

Another technique that has been attempted is removal of the polymethylmethacrylate with an ultrasonically vibrated osteotome. Such a technique is described in U.S. Pat. No. 4,248,232 by Engelbrecht. The osteotome is used for scooping out polymethylmethacrylate cement softened by the ultrasonic vibrations.

Other techniques involve use of long, thin osteotomes for cutting either the cement used for securing the prosthesis in the medullary canal or cancellous bone in the case of an ingrowth prosthesis. In effect, the osteotomes are long chisels which are tapped to disintegrate the cancellous bone or cement and free the prosthesis from the surrounding cortex. For example, in a paper entitled "Atraumatic Removal of a Well-Fixed Porous Ingrowth Hip Prosthesis," *Orthopedic Review*, Vol 15, No. 5, June 1986, page 387, Doctors McClelland, James and Simmons describe removal of a femoral component "by the use of an oscillating saw and long, thin osteotomes to carefully separate the prosthesis from its intra-medullary environment. This portion of the procedure was both tedious and somewhat time-consuming, but no iatrogenic damage to the cortical tube of the proximal femur resulted. After the proximal half of the prosthesis had been freed up in this manner, the prosthesis was then extractable, using multiple heavy hammer blows applied to vise grips attached to the end of a McReynolds-wedge extractor."

It is clear that faster and less traumatic techniques are desirable for removing components of prostheses inserted in the medullar canal. It is also desirable to provide quicker and easier techniques for implanting prostheses. In addition, there remains a need for a quick release connector for permitting the rapid connection and disconnection of surgical tool tips and extenders to a source of ultrasonic energy, which permits the efficient propagation of ultrasonic energy therethrough.

SUMMARY OF THE INVENTION

There is provided in accordance with one aspect of the present invention a junction for rapidly connecting and disconnecting ultrasonic surgical components for the transfer of ultrasonic energy across said junction from a source thereof to an ultrasonically activated working tip. The junction comprises a generally cylindrical male component having at least two axially-extending splines spaced apart by at least two axially-extending flats. A female component is provided having a generally cylindrical recess with at least two axially-extending flats and at least two axially-extending splines on the interior circumference thereof in a corresponding relationship with the male component.

The female component is adapted to receive and be rotated with respect to the male component to interlock the corresponding splines and to provide a relatively high compression Junction therebetween to enable an efficient transfer of ultrasonic energy. Preferably, axial compressions in excess of about 300 pounds will be achieved. More preferably, axial compressions in excess of about 600 pounds, and most preferably in excess of about 1,000 pounds will be achieved. In addition, the foregoing axial compressions are preferably achieved by a rotation of the male component with respect to the female component of approximately 90° plus or minus 10°.

In accordance with another aspect of the present invention, an ultrasonic medical tool is provided. The ultrasonic medical tool comprises an ultrasonic transducer, an ultrasonic energy activated tip, and at least one extender extending between the transducer and the tip for conducting ultrasonic energy from the transducer to the tip. The extender is connected to the tip by means of at least one junction of the type defined above.

In accordance with a further aspect of the present invention, there is provided a method for conducting a medical procedure, of the type using a plurality of different ultrasonic energy activated working tips. In accordance with the medical procedure method, an ultrasonic energy transducer is provided which is coupled to a first ultrasonic energy activated working tip by at least one junction of the type defined above. The transducer is activated to transmit ultrasonic energy to the tip, and at least a portion of the medical procedure is performed.

Thereafter, the first ultrasonic energy activated tip is removed by rotation of the tip with respect to the transducer. A second ultrasonic energy activated tip is thereafter selected, and coupled to the transducer by way of a rotation of the second tip with respect to the transducer. The medical procedure is thereafter continued, utilizing the second ultrasonic energy activated tip. Preferably, the medical procedure comprises the implantation or the removal of an endoprosthesis from the medullary canal. Alternatively, the medical procedure comprises the removal of cement from the medullary canal.

In accordance with a further aspect of the present invention, there is provided a method of removing cement or adhesive from the interior surface of the medullary canal. In accordance with the adhesive removal method, an ultrasonic transducer is coupled to an ultrasonic energy activated adhesive cutting tool. The coupling is accomplished by inserting a male component in communication with one of the transducer and the tool within a recess in communication with the other of the transducer and the tool, and rotating the tool with respect to the transducer through an angle of about 90°. The cutting tool is thereafter positioned in contact with the adhesive and activated so that the adhesive may be cut with the cutting tool.

These and other features and advantages of the present invention will become apparent from the detailed description of preferred embodiments which follows, when considered together with the attached drawings and claims.

BRIEF DESCRIPTION OF THE DRAWINGS

FIG. 3 is a schematic view of a medical device including a power supply and an ultrasonic transducer equipped for coupling to a femoral component as illustrated in FIG. 2;

FIG. 4 is a side view of a femoral component including rasp-like teeth;

FIG. 5 is a schematic illustration of an ultrasonic medical tool of the present invention showing a handpiece, an extender and a cement plug removal tool bit;

FIG. 6 is a perspective view of the extender of FIG. 5;

FIG. 7 is a partial cross-sectional view of the ultrasonic medical tool of FIG. 5 taken along line 7—7 illustrating two junctions of the present invention;

FIG. 8 is an exploded partial cross-sectional view of the junctions of FIG. 7;

FIG. 9 is an exploded perspective view of one of the junctions of FIG. 7, illustrating the generally cylindrical male component on the proximal end of a surgical tool having a pair of splines interrupted by a pair of flats;

FIG. 9a is a cross-sectional view of the junction of FIG. 9 taken along line 9a—9a.

FIG. 10 is an assembly perspective view of the junction of FIG. 9 with a male component inserted into a female component;

FIG. 11 is an assembly perspective view of the junction of FIG. 10 with the components rotated to engage corresponding splines of each component;

FIG. 12 is a cross-sectional view of the junction of FIG. 10 taken along lines 12—12;

FIG. 13 is a cross-sectional view of the junction of FIG. 11 taken along lines 13—13;

DETAILED DESCRIPTION

Figures 1, 2:
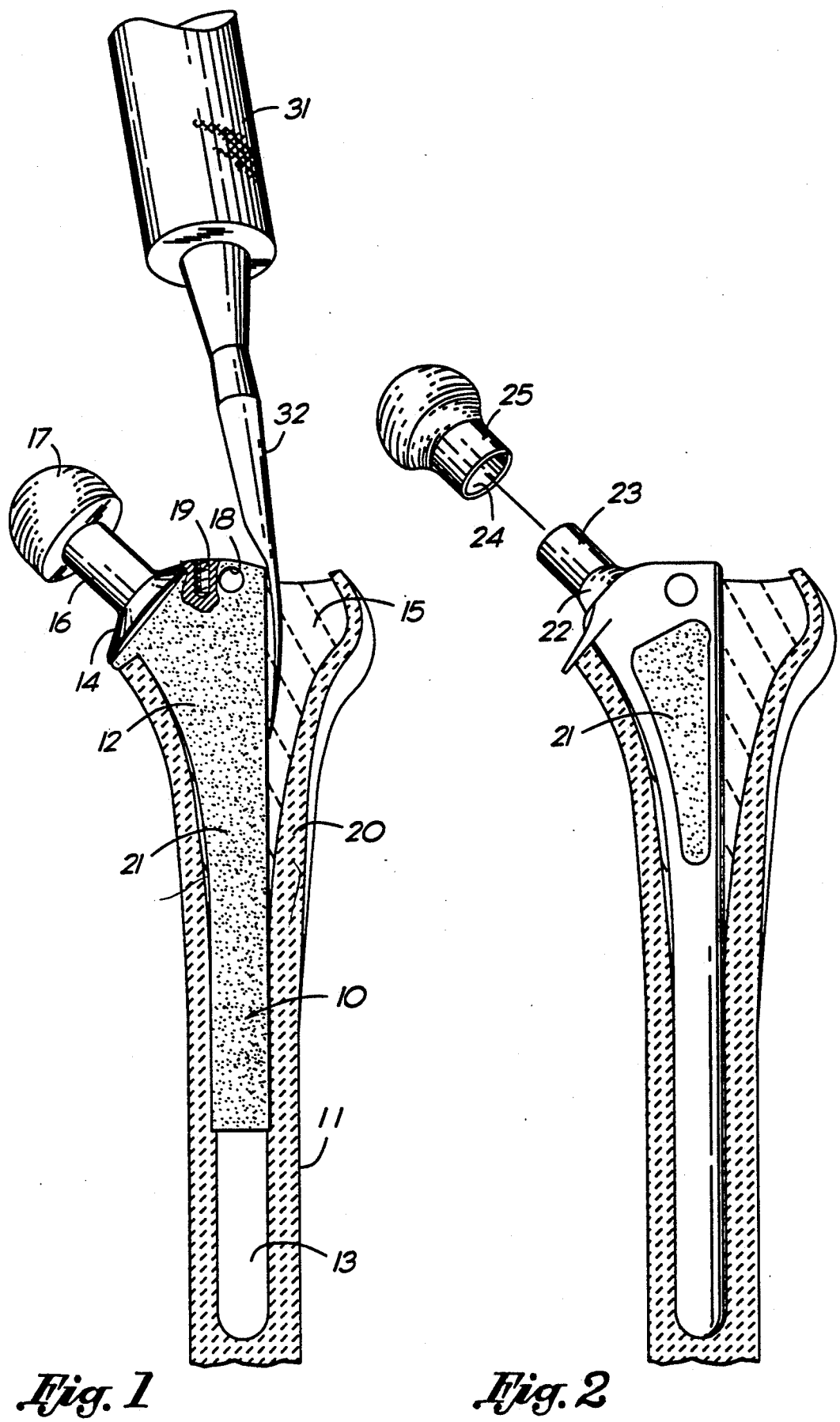
FIG. 1 is a side view partly in cross section of an exemplary femoral implant component of a hip replacement joint as implanted in a femur with an osteotome for disrupting cancellous bone.
FIG. 2 is a side view of another embodiment of a femoral component of a hip replacement joint implanted in a femur, with the head of the component exploded from the body.

FIG. 1 illustrates an exemplary femoral component 10 of a hip prosthesis joint implanted in the end of a femur which has the trochanter osteotomized. The body 12 of the prosthesis and at least a portion of the shank 13 which extends along the medullary canal have a porous surface. Such a porous surface is provided on the prosthesis by some manufacturers in the form of metal beads having the same composition as the prosthesis which are sintered onto the solid metal of the prosthesis. Other manufacturers employ a mat of metal wires sintered onto the surface. In either type, the porous surface portion provides a substrate into which growth of cancellous bone 15 may occur for rigidly securing the prosthesis to the femur. Some prostheses have a collar 14 which bears against the cortex 20 at the end of the femur. Collarless prostheses are also used.

A neck 16 connects a ball or head 17 to the body of the prosthesis. The spherical head provides the bearing engagement with the acetabular cup (not shown) secured to the patient's pelvis.

A transverse hole 18 extends through the prosthesis for engagement by a tool for extracting the prosthesis from the femur in the event a revision is required. In addition or alternatively, a threaded hole 19 is provided in the end of the body for receiving a tool which can provide a longitudinal force for withdrawing or inserting the prosthesis.

Another type of prosthesis as illustrated in FIG. 2 has a porous surface area 21 on the body for receiving ingrowth of cancellous bone for securing the prosthesis in the medullary canal. In the illustrated embodiment, the neck 22 of the prosthesis has a self-holding taper 23 at its proximal end for receiving a complementary female taper 24 in a head 25 which can thereby be removably secured to the prosthesis. A variety of self-holding tapers with different angles of taper and standard dimensions may be used. These include the Morse, Brown and Sharpe, Jarno, Sellers, Reed, American Standard and Metric tapers. Taper angles of 5% or less are customary. Self-holding tapers cause the shank, when seated firmly in the socket, to tend to stay in place by friction due to the small taper angle. For example, when the head is driven onto a Morse-type taper with a couple of mallet blows, it cannot be removed manually. A larger longitudinal force may be used for separating a self-holding taper.

A removable head for a prosthesis provides the opportunity for stocking heads with varying lengths of neck for fitting to a variety of standard bodies for mixing and matching to fit the prosthesis to an individual patient. For example, up to ten different dimensions of body may be matched with a dozen or so different heads with varying diameters and neck lengths.

For removing a prosthesis implanted in a femur, an ultrasonic transducer 26 (FIG. 3) is coupled to the prosthesis. At the end of the transducer there is a metal sleeve 27 having a socket 28 with a female self-holding taper matching the taper on the neck of the prosthesis. The intimate engagement of the self-holding taper provides high efficiency coupling of the ultrasonic vibrations from the transducer to the prosthesis.

The ultrasonic transducer may be any of a variety of known transducers. These may include electrostrictive, magnetostrictive or electromagnetic devices, as may be preferred by the equipment manufacturer. Each of these has certain advantages depending on the frequency range, amplitude of vibration, and power level.

The ultrasonic transducer is driven by an ultrasonic signal from a conventional power supply 29. Such power supplies typically permit the user to determine the frequency of oscillation and the power level of the ultrasonic signal sent to the transducer. For purposes of disrupting cancellous bone ingrown into the porous surface of a joint prosthesis, a frequency corresponding to a resonant frequency of the prosthesis is desirable for maximizing amplitude of vibration with a given signal strength. Some tuning of frequency for a particular prostheses implanted in bone may be employed in lieu of merely increasing signal strength. It is desirable to employ a frequency in the range of from about 20,000 to 40,000 Hertz, preferably around 25,000 Hertz.

For removing the prosthesis, the transducer is coupled to the self-holding taper on the prosthesis and the prosthesis is ultrasonically vibrated by applying a signal to the transducer. The vibration of the prosthesis disrupts cancellous bone at the surface of the prosthesis due to the impedance mismatch between the metallic prosthesis and the cancellous bone surrounding it. There is a substantial impedance mismatch between the portion of the prosthesis which does not have a porous surface and the surrounding cancellous bone, such as along the length of the shank, and the bone at the interface is readily disrupted. There is less of an impedance mismatch and also less energy transfer at the interface between the porous metal surface and the bony ingrowth. A somewhat higher energy input level is therefore required for disrupting cancellous bone adjacent to the surface of the porous ingrowth area.

After applying ultrasonic vibrations for several seconds, an attempt is made to withdraw the prosthesis. If the transducer is in the way, it may be removed before trying to withdraw the prosthesis to avoid damaging the transducer. In the event the prosthesis is not readily removed by application of pressure or moderate impact, the ultrasonic signal strength can be increased to try again to see if there has been adequate disruption of the cancellous bone at the interface with the porous surface.

Alternatively, the disruption of cancellous bone by the ultrasonic vibrations may be investigated by probing with a thin instrument passed along the body adjacent to the porous surface before an attempt is made to withdraw the prosthesis.

Some prostheses, such as the one illustrated in FIG. 1, have a head integral with the body rather than being connected thereto by a self-holding taper. The ultrasonic transducer may be coupled to such a prosthesis by way of a threaded hole, or a spherical socket may be used to mate with the spherical head and provide good energy transfer.

An alternative technique may be employed for disrupting cancellous bone adjacent to the porous surface of the prosthesis. According to this technique an ultrasonic transducer 31 (FIG. 1) is threaded onto a conventional osteotome 32 and the osteotome is inserted along the porous ingrowth surface of the prosthesis 10 for disrupting a narrow channel of cancellous bone. By repeatedly inserting ultrasonically vibrating osteotomes along different areas of the body of the prosthesis, sufficient cancellous bone can be disrupted to free the prosthesis from the bone and permit its withdrawal with limited trauma to the patient. This technique for disrupting cancellous bone may be used in areas readily accessible at the proximal end of the prosthesis and ultrasonic vibration of the entire prosthesis may be employed for disrupting cancellous bone adjacent to the distal end of the prosthesis.

It should be noted that disruption of the bone occurs at the impedance mismatch between the metal and the bone. There is sufficiently low energy transfer through the bone and other tissues to avoid significant damage to the cancellous bone or cortex remote from the interface. Preferably the energy level is kept low enough that there is insignificant disruption of cortical bone in places where the shank of the prosthesis contacts such bone.

When removing a porous ingrowth prosthesis by ultrasonically vibrating osteotomes, equipment similar to that described in the Engelbrecht patent, supra, may be employed, the disclosure of which is hereby incorporated by this reference. Osteotome blades are available with male threaded ends for attachment to handles or the like. The threaded end makes a convenient place for coupling an ultrasonic transducer to the osteotome. The threaded tip of a transducer may be placed in the threaded hole 19 in a prosthesis as illustrated in FIG. 1 for efficiently coupling the ultrasonic vibrations between the transducer and the prosthesis. The way of coupling the transducer to the osteotome is not of significance and other means may be employed. Coupling to the self holding taper of a prosthesis is preferred.

It will also be noted that the power levels required when a transducer is coupled to an osteotome are considerably less than when a transducer is coupled to the prosthesis itself, since the area of the interface at which cancellous bone is being disrupted is considerably different.

A technique for removing a prosthesis by ultrasonically vibrating it may also be employed where the prosthesis has a substantially smooth surface and is secured in the bone by a cement such as polymethylmethacrylate (PMMA). In such an embodiment the PMMA remains softened and can be readily disrupted while ultrasonic vibrations are being applied. When vibrations are discontinued, the PMMA may become more rigid. It is, therefore, desirable when removing a prosthesis which is cemented in place, to apply ultrasonic vibrations and a withdrawing force simultaneously. This assures that a minimum withdrawal force is used for withdrawing the component. Again, if the prosthesis is not removed readily with a withdrawing force which may be steady or in the form of impact, the power level may be increased until a reasonable withdrawing force is sufficient for withdrawing the prosthesis from the medullary canal.

After removing the femoral stem 10, the revision procedure further requires the removal of the PMMA from the femoral canal. By energizing various specialized tool bits with ultrasonic energy, the tools easily slice through the softened PMMA and separate the PMMA from the adjacent cancellous bone 15. A variety of ultrasonic energy-activated tool bits or tips can be used during the cement removal procedure. For example, a gouge can be used to debulk cement from a proximal area, a flat osteotome can be used to separate the cement from the cancellous bone, a slitter or a hoe can be used to slice through the cement, and a cement plug modification tool, such as a plug removal tool bit 44 shown in FIG. 5, can be used to remove a cement plug at the distal end of the femoral canal.

Thus, there has been provided in accordance with another aspect of the present invention a mechanical junction for facilitating the rapid attachment and removal of any of the plurality of tool bits during the course of a surgical procedure. In addition to permitting rapid connection and disconnection within the sterile field, the junction of the present invention achieves a high, evenly distributed compressive force to optimize propagation of ultrasonic energy from the transducer to a tool bit, while maintaining a relatively small outside diameter of the ultrasonic tool.

Referring to FIG. 5, there is illustrated an ultrasonic medical tool 40 comprising an ultrasonic handpiece transducer 42 and an ultrasonic energy-activated tool bit 44 coupled to the handpiece transducer 42 via an extender 46. A first junction 43 is illustrated at the proximal end 48 of extender 46, and a second junction 45 is illustrated at the distal end 49 of extender 46. As used herein, the words proximal and distal refer to proximity to the handpiece transducer which supplies the ultrasonic energy to the tool bit.

Preferably, the location of each junction between the transducer 42 and tool bit 44 occurs at an antinode of the ultrasonic oscillation to minimize mechanical stress at the junctions. Thus, for example, junctions in an assembled tool will preferably be distanced apart by a whole number multiple of the distance $\lambda/2$, where $\lambda$ equals the wavelength for a given frequency of ultrasonic oscillation. Preferably, the junctions will be located at multiples of $\lambda/2 \pm 20\%$ along the length of the assembled instrument. It should be noted that the junction(s) can occur at the nodes of oscillation so long as the junction is designed to withstand the increased mechanical stress at the nodal position. Due to the desirability of maintaining a relatively small tool diameter, however, together with efficient propagation, it is preferred that the junctions occur precisely at or approximately at antinodal positions.

For the cement removal process, it is desirable to employ a frequency in the range of from about 10,000 to about 100,000 Hz, preferably about 20,000 to about 60,000 Hz, and most preferably around 40,000 Hz. Thus, for example, in a most preferred embodiment of the present invention, detailed infra, antinodes are spaced approximately 2.4 inches apart in a 0.260 inch diameter extender comprising the preferred titanium alloy and operated at approximately 40 kHz.

The length of the tool bit 44 and the length and number of extenders 46, discussed infra, is also influenced by its intended use. For example, when working inside the femoral canal, the length of the tool 44 together with the extender(s) 46 should allow the tool 44 to be appropriately positioned within the canal, but not so long as to impair the surgeon's ability to maneuver the tool. Generally, the depth of the femoral canal in a human adult is generally not greater than on the order of about 20 inches.

Preferably, the length of the tool 44 is also influenced by the intended operating frequency for that particular tool. For most tools, maximum longitudinal oscillation at the distal end of the tool bit 44 is desirably obtained by positioning the tip to coincide with an antinode of the ultrasonic oscillation. Thus, as discussed above, the length of the tool 44 generally will equal a whole number multiple of $\lambda/2$ for the ultrasonic frequency employed and preferably will equal $\lambda/2$. For example, in a most preferred embodiment, for use in the cement removal procedure, the tool length will equal about 2.4 or 4.8 inches for operation at 40,000 Hz.

It is preferred that the outer diameter of each surgical component match the outer diameter of the component intended to be joined immediately adjacent thereto to eliminate surface irregularities. When working in environments where liquid such as blood or saline surrounds the tool, the transmitted ultrasonics can produce cavitations at projecting surfaces. Cavitation at areas other than the tool bit tip are undesirable because of the ultrasonic energy loss and because of the erosion effect on the surgical components. Thus, it is preferred that the outside diameters of the joined components be substantially identical at their interface so as to provide a substantially uniform external dimension through each junction.

The overall diameter of the tool bit 44 or extender 46 is limited only by the environment of its intended use. For example, in replacing the femoral component 10 of a hip joint replacement, the tool bit 44 diameter is limited by the interior diameter of the femoral canal which typically ranges between about 0.25 to about 0.75 inches. Preferably, the tool bit 44 diameter is sized even smaller to allow for the concurrent insertion into the femoral canal of additional apparatus such as irrigation and aspiration tubes, as well as a fiber optic visualization system.

The overall diameter also depends upon the configuration of the tool bit 44 tip. For example, a gouge may have a wider overall diameter than a slitter. In general, the diameter of the tool bit at the junction is less than about ½ inch and preferably less than about ⅜ inch. More preferably, the junction diameter is about 0.260 inches.

The diameter of the tool bit 44 along its axial length can be tailored to produce a desired longitudinal oscillation or stroke at a tool tip 51. As known in the art, by changing the diameter of the tool along its length, the amplitude of the oscillation will also change. Thus, by decreasing the tool diameter either gradually (i.e., in a Gaussian shape) or by stepped diameter, the amplitude can be adjusted to achieve a desired stroke at the tool tip 51.

In general, the stroke of the tool tip 51 should not be so great as to overstress the tool 44. For example, in a most preferred embodiment of the present invention, with the diameter equal to 0.260 inches in a titanium alloy tool, the stroke should not exceed about 0.004 inches peak-to-peak. It is understood, however, that the shape of tool or the tempering of the material comprising the tool can increase its ability to withstand greater stress at larger strokes. But it has been found that stroke lengths greater than about 0.008 inches peak-to-peak do not appreciably increase the effectiveness of the tool to remove cement or fashion the cancellous bone.

More preferably, the longitudinal profile of the tool should be designed to produce a stroke length of from about b 0.001 inches to about 0.004 inches, and most preferably a stroke length of about 0.002 inches for the majority of tool tip 51 configurations. For tool tips with relatively large surface area, the stroke is preferably larger, such as in the range of 0.002 to 0.004 inches peak-to-peak.

Referring to FIG. 5, the illustrated tool bit 44 comprises a barb tip tool bit having a generally radially symmetrical body portion 70, which, preferably, is substantially cylindrical. A generally arrow-shaped opposing pair of projections 72 are positioned at the distal end of the tool bit 44 which ramp radially inwardly in the distal direction to form a sharp point. Preferably, the tool bit 44 additionally includes a second opposing pair of arrow-shaped projections 74 disposed on the proximal side of the first projections 72. The tool bit 44 additionally preferably comprises a substantially radially symmetrical distal portion 76 of reduced exterior dimension positioned between the projections 74 and the cylindrical body portion 70 to amplify the ultrasonic oscillations at the distal end of the tool bit, as known in the art and discussed above.

In use, the plug removal tool bit illustrated in FIG. 5 is inserted under ultrasonic energy into the cement plug which remains in the bottom of the femoral canal following removal of a cemented prosthesis. Softened cement flows up over the ramped surfaces and behind the barb, thereby enabling manual retraction of the tool to pull the cement plug loose from the femoral canal.

Figure 14:
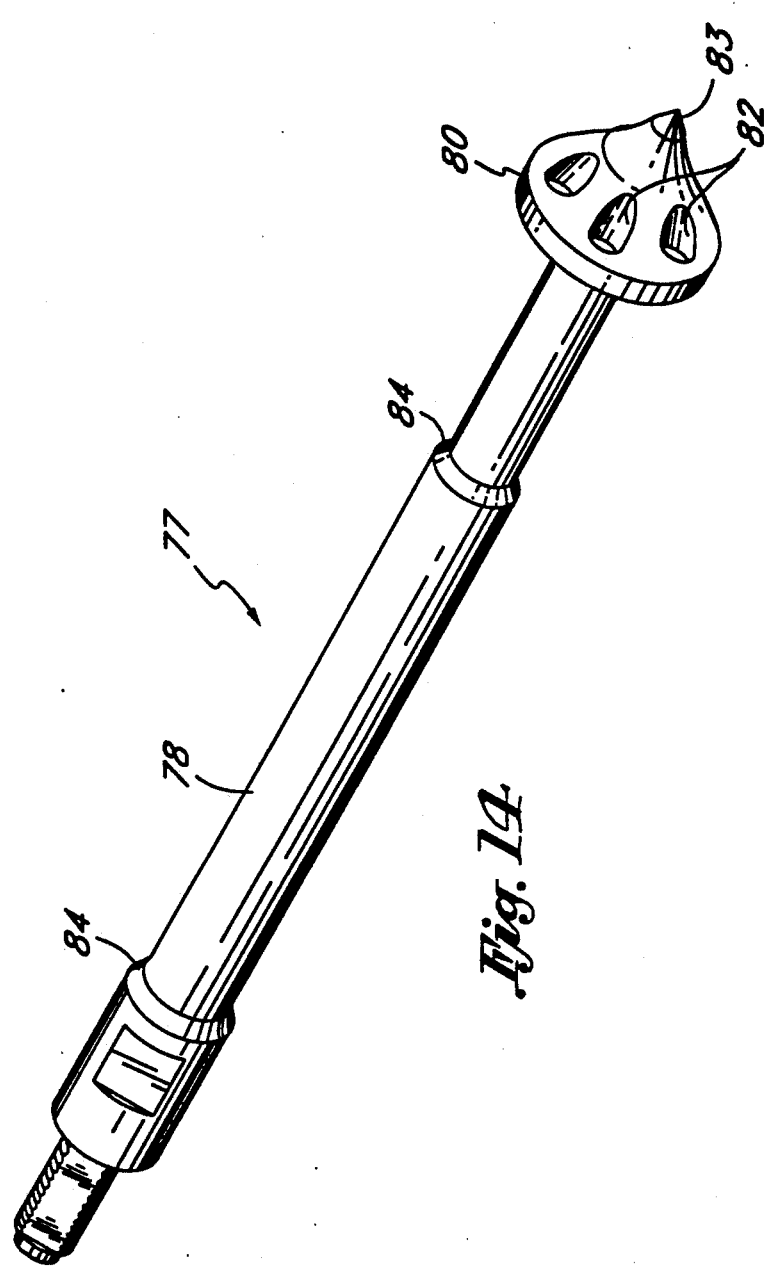
FIG. 14 is a perspective view of a disk drill tool tip.

Although FIG. 5 illustrated the tool bit 44 as being a barb tip tool bit, it is understood that other tool configurations, such as a gouge, slitter or hoe, can be used as well. For example, FIG. 14 illustrates a Poly Methyl Methacralate modification tool 77. The disk drill tool bit 77 comprises an elongate body portion 78 and a radially outwardly extending annular flange 80 positioned at the distal end of the tool bit 77. The flange 80 is provided with a plurality of apertures 82 extending therethrough in the longitudinal direction. Preferably, the annular flange 80 is inclined radially inwardly in the distal direction to produce a substantially cone shaped working tip.

In use, the conical tip 83 is embedded in the cement plug under ultrasonic energy with some softened cement extruding through the apertures 82. The tool is mechanically withdrawn from the canal to extract the cement extruded through the apparatus. Preferably, the apertures 82 are sized and positioned to optimize the extraction of the cement, while at the same time retaining sufficient structural integrity to withstand the combination of ultrasonic energy and physical manipulation by the clinician. Generally, the tool comprises from about 4 to about 20 apertures 82 evenly spaced about the circumference of the conical tip 80. Preferably, about six to about ten apertures are provided.

It is also preferred that the body 78 have one or more diameter reductions 84 to amplify the ultrasonic oscillations at the distal end of the tool, as discussed above.

The ultrasonic energy conducting extender 46 will be understood by reference to FIGS. 5 and 6. The extender 46 enables the tool bit 44 to be spaced apart from the transducer 42 and acoustically couples the tool bit 44 to the transducer handpiece 42, as shown in FIG. 5. The length of the extender 46, like the tool bit 44, is influenced by the operating wavelength and by its intended use.

Preferably, the extender length coincides with the wavelength of the ultrasonic oscillation to position the handpiece/extender junction and the extender/tool junction at antinodes of the oscillation. More preferably, the length of the extender 46 equals 2.022 inches, 4.453 inches or 6.849 inches, plus or minus 20%, preferably plus or minus less than 10%, more preferably plus or minus less than 5% and most preferably plus or minus no more than about 1%.

It is also preferred that the extender 46 includes a stepped diameter 47, as shown in FIG. 6, to amplify the ultrasonic energy, as discussed above in the context of the tool diameter. However, for successive extenders, it is understood that extenders may be provided having a substantially uniform cross-sectional dimension throughout.

Referring to FIG. 8, the tool bit 44 connects to the extender 46 via a second junction 45. Likewise, the extender 46 connects to the handpiece 42 via a first junction 43. It is contemplated that the structure of the first and second junctions 43, 45, apart from diameter, will be substantially identical, and the discussion herein of one will be understood as applying equally to both, unless specified to the contrary.

FIGS. 7–9 illustrate the junctions 43, 45 which comprise a generally cylindrical male component 52 and a tubular female component 54 comprising a generally cylindrical recess 56 adapted to receive the male component 52. These components quickly connect by inserting the male component 52 into the female component 54 and rotating one component with respect to the other component, preferably through a relatively short rotational arc, and optimally about ninety° plus or minus 10°.

When joined, the junction 43 produces a relatively high axial compression force, which is preferably uniformly distributed symmetrically about the contact surfaces between the two components to optimize the transfer of ultrasonic energy across the junction 43. Non uniform distribution of the axial compression force about the longitudinal axis of the junction 43 tends to decrease the efficiency of the transfer of energy across the junction 43, and can cause unwanted transverse motion (whipping) and may lead to premature mechanical failure.

Although FIGS. 6 through 12 illustrate the male component 52 extending in a proximal direction, it is understood that the relationship of the male and female components can be reversed.

Referring to FIGS. 8 and 9, the male component 52 comprises at least two axially extending splines 58 spaced apart by at least two axially extending flats 60. Preferably, the male component 52 comprises two diametrically opposed splines 58 and two diametrically opposed flats 60, alternatively positioned around the circumference of the component, as seen in FIG. 9.

Each spline 58 comprises a plurality of external threads 62 preferably configured in accordance with the American National Standard for Unified Threads ("UN"). It will be understood that other thread configurations, such as the American National Standard Acme Screw Threads ("Acme"), can be used as well. It has been found preferable, however, to employ the UN thread design instead of others, such as the Acme thread design, primarily for manufacturing ease.

Advantageously, the thread pitch and the pitch diameter of the threads 62 and the length of the splines 58 are selected to produce high axial compression between the components without structural failure. It is also preferable to select a generally standard thread for manufacturing convenience. Additionally, the threads must engage to produce high axial compression with little rotation. Preferably, circumferentially, 75% of the threads engage with rotation of no more than about 90° plus or minus 10°. For example, in one preferred embodiment the splines 58 comprise a series of 10-28 UNS-2A threads along a length of 0.315 inches, and in another embodiment, the splines 58 comprises a series of ¼-28 UNF-2A threads along a length of 0.435 inches. In general, the spline preferably comprises about 12 interrupted threads.

In general, the junction 43 has a minimum of 45° of total engagement between the spline threads to produce the high axial compression without mechanical failure. Preferably, the junction has an engagement between about 90°-179° and most preferably about 173° (48% of 360°=172.8°). Thus, in a most preferred embodiment, the sum of the lengths of the threads 62 on the male component measured in a circumferential direction preferably range from 90° to 179°, and more preferably equal 173°.

The circumferential length of each spline thread 58 (i.e., the circumferential width of each spline) depends upon the number of splines 58 employed. For example, in a most preferred embodiment having two splines, the length of the thread 62 in a single spline along the circumferential direction range between 45° and 89.5°, and preferably equal 86.5°.

The female component 54 likewise comprises at least two axially extending splines 64 and at least two axially extending flats 66, disposed on the recess circumference 56 in a corresponding relationship with the flats and splines on the male component, as best seen in FIGS. 7, 12 and 13. Preferably, the female component 54 comprises two diametrically opposed splines 64 and two diametrically opposed flats 66 alternatively positioned around the circumference of the recess 56, as best seen in FIG. 12. Each spline 64 comprises a plurality of internal threads 68 configured to match and engage with the threads 62 on the male component 52.

As discussed above, the sum of the length of the threads 68 around the circumference of the recess 56 is preferably not less than about 90° and not greater than about 179°, and most preferably equal 173°. Each spline thread length depends upon the number of splines employed. For example, in a most preferred embodiment having two splines 64, the threads 68 of each spline 64 extend around the circumference of the recess 56 for at least approximately 45°, but less than approximately 89.5°, and preferably equal 86.5°.

The two splines 64 and two flats 66 alternately disposed on the interior circumference of the female component recess 56 provide an axial key-way 67 for receiving the two opposing splines 58 on the male component 52, as shown in FIG. 12. The male component 52 is inserted into the recess 56 of the female component 54 and rotated to interlock the corresponding splines on the male and female components, as shown in FIG. 13. It is desired that minimum rotation of one component with resect to the other component will produce a junction which achieves a relatively high efficiency of energy transmission therethrough.

In general, it has been found that a high compression across the junction symmetrically distributed about its longitudinal axis optimizes energy propagation. Preferably, the thread 62, 68 design of the junction 50 produces greater than about 300 pounds of axial compression force between the components with rotation of about 90°±10%. More preferably, a compression in excess of about 500 pounds will be achieved. Axial compressions of about 675 lbs. for a junction having an outside diameter of about, 0.260 have been measured. Compressions in excess of about 1500 lbs. have been measured with an outside diameter of 7/16 inch, and in excess of about 2300 lbs. have been measured for diameters of 0.750 inches. As a result of higher compression, the ultrasonic pressure wave propagates across the junction with minimal energy loss.

It is preferred that the points of contact between the two joined surgical components be symmetric about the longitudinal axis of the male component 52 to uniformly distribute the compression force about the junction 43 in the radial direction. As a result, the ultrasonic oscillation maintains its propagation along the longitudinal axis of the joined surgical components without deflection from that axis. If deflection occurs, the tool will tend to whip resulting in undesired heat build-up and loss of energy at the tool tip 51.

In this regard, the female component 54 preferably additionally comprises an annular engagement surface 86 on the proximal end thereof which contacts a corresponding annular engagement surface 88 of the male component 52. Preferably, the engagement surface 86 of the female component 54 extends radially outwardly along a plane substantially perpendicular the axis of the internal recess 56, and the engagement surface 88 of the male component 52 extends radially outward along a plane substantially perpendicular to the axis of the male component 52. Referring to FIG. 7, as the splines 58, 64 interlock, the two components draw together to force the engagement surfaces 86, 88 against each other, resulting in an axial compression force across the junction 50.

Preferably, the engagement surfaces 86, 88 are smoothly polished to produce a substantially liquid-tight seal between the components as the surfaces abut. In addition to optimizing energy propagation, a liquid-tight seal reduces cavitation erosion of the components at the junction 50 and thereby extends the life of each component.

In a preferred embodiment, the female component 54 additionally comprises an axially extending, generally cylindrical counterbore 90 at the distal end of the recess 56 for receiving a generally cylindrical shank barrel 92 on the proximal end of the male component 52. The counterbore 90 and the shank barrel 92 are preferably centered with respect to the longitudinal axis of the male component 52. Preferably, the shank barrel 92 smoothly fits into the counterbore 90 to center the female component 54 with respect to the male component 52.

Advantageously, the male component 52 further comprises an undercut region 94 positioned between the engagement surface 88 and the spline 58 so that the spline threads 62 are fully formed (i.e., no run-out region). As a result, the splines 58 can be reduced in overall length, as will be understood in the art.

Referring to FIG. 8, the female component 54 preferably additionally includes a generally cylindrical pilot recess 96 for receiving a corresponding generally cylindrical tip barrel 98 at the proximal end of the male component 52. Preferably, the diameters of the pilot recess 96 and the tip barrel 98 substantially coincide with the minor diameter of the threads 62, 68. Advantageously, the pilot recess 96 and the tip barrel 98 are centered about the longitudinal axis of the male component 52 for optimizing the concentricity of the engagement surfaces 86, 88 between the components to optimize the longitudinal transfer of ultrasonic energy through the junction 43.

To facilitate rapid interconnection between the components, the female component 54 preferably additionally comprises an annular internal chamfer 100 and the male component 52 additionally comprises an annular tip chamfer 102. When the male component 52 is inserted into the female component 54, the chamfers 100, 102 ease the insertion by funneling the components together. Additionally, the edges of the leading spline threads 62 of the male component 52 preferably include a chamfer 104 to ease the engagement between the splines 58, 64 of the male component 52 and female component 54.

Referring to FIGS. 10 through 13, it is preferred that the surgical components include alignment arrows 106 etched on the exterior surface of the components to aid in the connection process. By aligning the arrows, the splines 58 of the male component 52 align with the key-way 67 of the female component 54, as seen in FIGS. 10 and 12. By rotating the components as shown in FIG. 11, the splines 58, 64 of the two components interlock, as shown in FIG. 13. Flat opposing surfaces are provided on the exterior surface of all parts to receive a wrench to facilitate tightening and untightening of the junctions.

Those skilled in the art can manufacture the disclosed junction 43 by processes known in the art. For example, the generally cylindrical male component 52 and the shank barrel 92 thereto can be cut into an end of the shank of a surgical component, such as the extender 46 or the tool bit 46. The threads 62 can either be cold rolled onto the cylinder or preferably machine cut into the cylinder. The flats 64 can then be milled onto the component thereby interrupting the threads 62. Finally, the tip barrel 98 can be cut onto the distal end of the male component 52 such as by lathing operations well known in the art and the chamfers 102, 104 similarly added thereto.

The recess 56 of the female component 54 can be made by drilling the pilot hole recess 96 into the end of a surgical component. The counterbore 90 then can be milled and a portion of the pilot hole 96 tapped with the appropriate internal threads by processes known in the art. The flats 66 can be milled and broached into the recess 56 thereby interrupting the threads 68 on the recess 56 wall. Finally, the internal annular chamfer 100 can be drilled or milled to form a smooth transition from the counterbore 90 to the threaded recess 56.

The tool bits 44 and extenders 46 herein can be manufactured from any of a variety of materials known in the art. Preferably, high quality factor materials are used due to their known superiority in propagating ultrasonic energy. More preferably, a 400 series stainless steel or titanium is used because of their relative biocompatibility and their strength. Most preferably, a high grade titanium, such as Ti-6A1-4V alloy (aircraft grade 5), AA sonic inspected, is used.

An ultrasonic technique may also be employed for implanting an original or a replacement prosthesis during revision surgery. The preparation of a cavity in which a prosthesis is placed can be tedious and careful shaping of the cavity is important so that a tight fit is obtained. This is particularly significant for implantation of prostheses having porous surfaces for ingrowth of cancellous bone. At present such a cavity is formed by drilling and reaming to form a cavity of roughly the right shape and size and then finishing the cavity with a rasp or series of rasps complementary to the shape of the prosthesis, which are hammered or pressed into the medullary canal.

In practice of this invention at least the final reaming of the cavity is done by ultrasonically vibrating an object having the same shape as the prosthesis, with sufficient energy to disrupt cancellous bone, and pressing the ultrasonically vibrating object into the cancellous bone for forming a cavity complementary to the prosthesis. Preferably the object has rasp-like teeth which further aid in disrupting cancellous bone so that the object can be pressed into the cavity without excessive force which could fracture the cortex.

The object employed for forming a cavity in the cancellous bone complementary to the prosthesis may be a rasp that is inserted and temporarily left in place for testing and other procedures before the prosthesis is implanted. Preferably the object comprises the prosthesis itself. Thus, as illustrated in FIG. 4, a prosthesis 36 such as the femoral component of a hip joint has a plurality of rasp-like teeth on surface areas 37 on at least the tapering body portion of the prosthesis. An exemplary size for the rasp-like teeth is about 400 micrometers peak-to-peak. An ultrasonic transducer 38 is coupled to the self-holding taper 39 on the neck of the prosthesis as hereinabove described. As the prosthesis is ultrasonically vibrated by the transducer, it is pressed into the cavity and the teeth cut cancellous bone until the prosthesis fits tightly in the cavity. The transducer can then be removed and the prosthesis left in the cavity so formed.

It is not important that the scarf produced by the teeth on the prosthesis be removed from the cavity. On the contrary, it is not unusual to pack a portion of the cavity with fragments of cancellous bone and tissue removed in forming the cavity to assure a tight fit of the prosthesis. Such materials appear to promote growth of cancellous bone and may enhance fixation of a porous ingrowth prosthesis in the cavity. It is desirable to employ teeth with a spacing from about 50 to 400 micrometers since that is appropriate for ingrowth of cancellous bone. Thus, the newly grown cancellous bone between the teeth tends to secure the prosthesis in the cavity. In other words, the teeth are analogous to the porous surface on conventional ingrowth type prostheses.

Although limited embodiments have been described and illustrated herein, it will be readily appreciated by those skilled in the art that there may be many modifications and variations of practice of this invention. For example, although coupling the ultrasonic transducer to the self-holding taper on a prosthesis is particularly desirable, any of a variety of coupling means may be employed. As should already be apparent from the description, these techniques may be employed in combination with other conventional techniques for loosening and removing a prosthesis from a joint.

Further, although described in the context of a hip joint replacement, it will be apparent that similar techniques may be used with implants of shoulder joints, knees and the like, or with pins used for reinforcing bone. For example, ultrasonic vibrations may be used for implanting the keel of the tibial component of a knee joint. Ultrasonic vibration of a rasping object may be used for final shaping of the cavity for an acetabular cup. It is, therefore, to be understood that within the scope of the appended claims, this invention may be practiced otherwise then as specifically described.

It is claimed:

1. An apparatus for conducting a medical procedure comprising:
   a first ultrasonic medical component;
   a second ultrasonic medical component; and
   a junction for rapidly connecting and disconnecting said first ultrasonic medical component from said second ultrasonic medical component for the transfer of ultrasonic energy across said junction, said junction comprising:
   a first abutment surface connected to said first medical component and positioned substantially symmetrically about said longitudinal axis of said first medical component;
   a second abutment surface connected to said second medical component and positioned substantially symmetrically about said longitudinal axis of said second medical component;
   a generally cylindrical male component comprising at least two axially extending splines spaced apart by at least two axially extending flats, said male component being connected to said first abutment surface; and
   a female component comprising a generally cylindrical recess having at least two axially extending flats and at least two axially extending splines on the circumference of the recess in a corresponding relationship with said at least two flats and at least two splines on said male component, said female component being connected to said second abutment surface;
   said female component adapted to receive said male component and to rotate with respect thereto to interlock the corresponding splines on the male and female components, said interlocking splines of said male component and said female component comprising means for compressing said first and second abutment surfaces together with a sufficient axial compressive force to efficiently transfer ultrasonic energy between said first and second ultrasonic medical components.

2. An apparatus as in claim 1, wherein said male component comprises two diametrically opposed splines and two diametrically opposed flats, said splines and flats alternately positioned around the circumference of said component.

3. An apparatus as in claim 1, wherein said female component further comprises a generally cylindrical pilot recess for receiving a corresponding generally cylindrical tip barrel on said male component for optimizing the concentricity between said male and female components of said junction to thereby optimize the transfer of ultrasonic energy therethrough.

4. An apparatus as in claim 3, wherein said tip barrel terminates at its proximal end at said at least two splines, and terminates at its distal end at an annular tip barrel chamfer for facilitating rapid interconnection of said male and female components.

5. An apparatus as in claim 1, wherein said female component further comprises an axially extending, generally cylindrical counterbore at the proximal end of said recess for receiving a generally cylindrical shank barrel on the proximal end of said male component.

6. An apparatus as in claim 5, wherein the generally cylindrical counterbore on said female component is further provided with an annular internal chamfer for facilitating rapid interconnection of said male and female components.

7. An apparatus as in claim 1, wherein said male component and said female components are rotated no more than about 90°±10° with respect to each other to achieve a compressive force in excess of about 675 pounds.

8. An apparatus as in claim 1, further comprising an annular engagement surface on the proximal end of said female component, extending in a plane substantially perpendicular to the axis of said internal recess, for engaging a corresponding annular engagement surface near the proximal end of said male component, which extends radially outwardly along a plane substantially perpendicular to the axis of said male component.

9. An apparatus as in claim 8, wherein a rotation of said male component with respect to said female component of within the range of about 80° to 100° creates a compressive force between said female engagement surface and male engagement surface in excess of about 300 pounds.

10. An apparatus as in claim 9, wherein the junction between said female engagement surface and male engagement surface provide a substantially fluid-tight seal.

11. An apparatus as in claim 1, wherein each of said splines on said male component comprises a plurality of external threads configured in accordance with the American National Standard for Unified Threads having a pitch of 28 threads per inch.

12. An apparatus as in claim 11, wherein said external threads are 10–28 UNS.

13. An apparatus as in claim 11, wherein said external threads are ¼–28 UNF.

14. An apparatus as in claim 2, wherein the width of each spline as measured about the circumference of said cylindrical male component is between approximately 45° and approximately 88.5° of the circumference of said male component.

15. An apparatus as in claim 1, wherein the sum of the widths of said splines as measured about the circumference of said cylindrical male component is between about 90° and 179° of the circumference of said male component.

16. An apparatus as in claim 1, wherein two splines and two flats are disposed on the interior circumference of said female component in opposing relationship, thereby providing a key way axially therethrough for receiving two opposing splines on said male component.

17. An ultrasonic medical tool comprising:
an ultrasound transducer;
an ultrasonic energy activated tip;
at least one extender extending between said transducer and said tip for conducting ultrasonic energy from said transducer to said tip; and
a junction connecting said extender to said tip, said junction comprising;
 a male component comprising a generally cylindrical shank extending from and generally normal to an engagement surface, said shank comprising two axially extending splines spaced apart by two axially extending flats, each spline comprising a series of threads having a substantially uniform thread pitch; and
 a female component comprising a generally cylindrical recess circumscribed by an engagement surface, said recess comprising two axially extending flats and two axially extending splines on the circumference of said recess in a corresponding relationship with said splines and flats on said male component, said recess adapted to receive said male component and to rotate with respect thereto to interlock the corresponding splines on said male and female component, said splines of said female component comprising a series of threads having a substantially uniform thread pitch substantially matching that of said male component splines, said interlocking splines of said male component and said female component being configured to produce an axial compressive force between said corresponding engagement surfaces of said male and female components in excess of about 300 pounds with said female component being rotated with respect to the male component through an angle within the range of about 80° to 100°.

18. A medical apparatus, comprising:
an ultrasonic transducer;
an ultrasonic medical component; and
a junction for rapidly connecting and disconnecting said ultrasonic medical component from said transducer, said junction comprising:
 a male component comprising a generally cylindrical projecting structure having a shank barrel, a tip barrel, two diametrically opposed splines and two diametrically opposed flats, said splines and flats alternately positioned around said structure circumference and disposed between said shank barrel and said tip barrel; and
 a female component comprising a generally cylindrical recess, a counterbore circumscribing said recess, a pilot recess positioned adjacent to said recess and opposite of said counterbore, a pair of diametrically opposed splines and a pair of diametrically opposed flats, said splines and flats alternately positioned around said recess circumference and disposed between said counterbore and said pilot recess,
 said male component adapted to slide into said female component and to rotate with respect thereto to interlock the corresponding splines on said male and female components, said tip barrel snugly fitting within said pilot recess and said shank barrel engaging said counterbore to axially align said ultrasonic surgical components.

19. The junction as in claim 1, wherein the said first and second ultrasonic surgical components are selected from the group consisting of an ultrasound transducer, an ultrasonic energy activated tip and an extender.

20. The junction as in claim 17, wherein said ultrasonic transducer produces sonic oscillations which propagate along the length of an assembly formed by at least one extender and said tip interconnected via said junction, said junction being positioned to coincide with a location of an antinode of the sonic oscillation.

21. A medical apparatus, comprising:
an ultrasonic transducer;
an ultrasonic medical component; and
a male connector component of a junction used to connect said ultrasonic medical component to said ultrasonic transducer, said male component adapted to slidably engage a female component of said junction and to rotate into an interlocking position therewith, said male component comprising:
 a shank barrel configured to engage a correspondingly shaped recess defined by the female component, said shank barrel being connected to an end of said ultrasonic medical component; and
 a stud member having a tip barrel and an interrupted threaded portion, said threads interrupted by a pair of diametrically opposed longitudinal flats, said threaded portion being disposed between said shank barrel and said tip barrel, said tip barrel being configured to engage a correspondingly shaped recess defined by the female component, said shank barrel and said tip barrel being concentrically positioned about a longitudinal axis of the shank to concentrically position the male component within the female component when engaged.

22. A medical apparatus, comprising:
an ultrasonic transducer;
an ultrasonic medical component; and
a female component of a junction used to connect said ultrasonic medical component to said ultrasonic transducer, said female component adapted to slidably engage a male component of said junction and to rotate into an interlocking position therewith, said female component comprising:
 an engagement surface to abut a similar surface of said male component when engaged;
 a recess comprising a threaded portion interrupted by a pair of diametrically opposed longitudinal flats;
 a counterbore being configured to snugly receive a portion of said male component, said counterbore being disposed between said engagement surface and said threaded portion; and
 a pilot recess configured to snugly receive a portion of said male component and disposed adjacent to said recess opposite of said counterbore, said counterbore and said pilot recess concentrically positioned about a longitudinal axis of said recess to concentrically position the male component with respect to the female component when engaged.

* * * * *